United States Patent [19]

Perrier et al.

[11] Patent Number: 5,773,014
[45] Date of Patent: Jun. 30, 1998

[54] COMPOSITIONS AND METHODS FOR INHIBITING THE FORMATION OF UNWANTED SKIN PIGMENTATION

[75] Inventors: Eric Perrier, Les Cotes D'Aarey; Delphine Rival, Lyons, both of France

[73] Assignee: Bioetica, Inc., Portland, Me.

[21] Appl. No.: 710,165

[22] Filed: Oct. 7, 1996

[51] Int. Cl.$^6$ .................................................. A61K 7/00
[52] U.S. Cl. ........................ 424/401; 424/58; 424/59; 424/195.1; 424/62; 424/40; 514/476; 514/783; 514/887
[58] Field of Search ........................ 424/59, 58, 195.1, 424/62, 401; 514/476, 783, 887

[56] References Cited

U.S. PATENT DOCUMENTS 5,607,980  3/1997  McAtee et al. .................. 514/476

FOREIGN PATENT DOCUMENTS 04346911  12/1992  Japan .
05058870   3/1993  Japan .
07097311   4/1995  Japan .
08020525   1/1996  Japan ................................ 514/861

OTHER PUBLICATIONS (Abstract) Tezuka, Body Shampoos Containing Smechle Group Minerals and Lubricants to Improve Skin Conditions, Jan. 23, 1996.

Primary Examiner—Thurman K. Page
Assistant Examiner—D. Faulkner
Attorney, Agent, or Firm—Cesari and McKenna, LLP

[57] ABSTRACT

Compositions for inhibiting the formation of unwanted skin pigmentation combine high tyrosinase blocking capabilities with stability in cosmetic preparations, absence of significant cytotoxic effects and synergy of action. The active components of the compositions include extracts of certain selected plants, namely, mulberry, saxifrage, grape and scutellaria root; and, preferably, ethylenediaminetetraacetic acid (EDTA). These ingredients are combined with various cosmetically acceptable carriers to produce cream and lotion formulations capable of whitening skin safely and effectively.

20 Claims, 1 Drawing Sheet

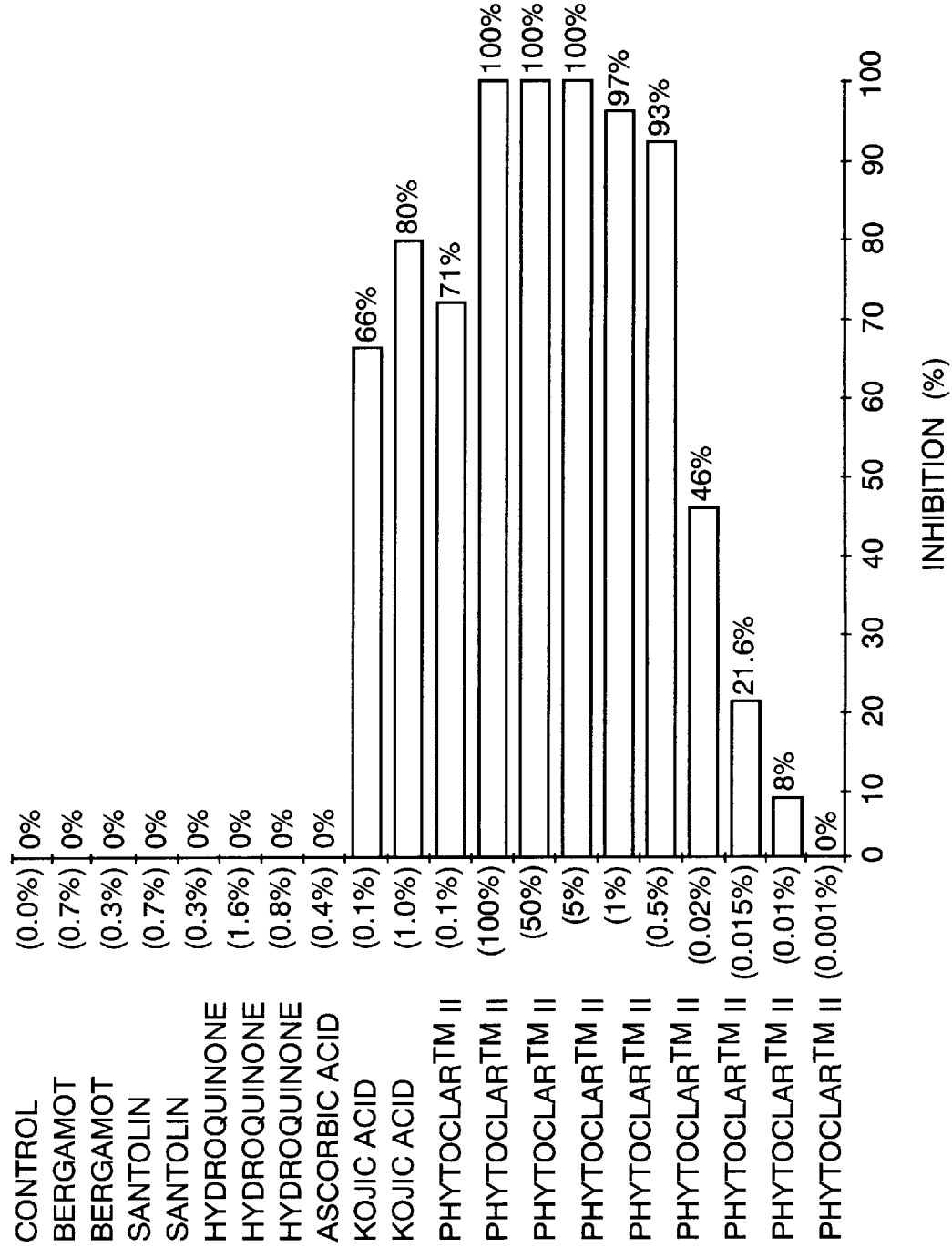

COMPOSITIONS AND METHODS FOR INHIBITING THE FORMATION OF UNWANTED SKIN PIGMENTATION

FIELD OF THE INVENTION

The present invention relates generally cosmetic preparations, and in particular to compositions for reducing or eliminating the formation of unwanted skin pigmentation through inhibition of melanin synthesis.

BACKGROUND OF THE INVENTION

Skin pigmentation occurs in various specialized cells through the synthesis of melanin. The primary purpose of melanic pigmentation is to absorb solar radiation and thereby protect the body against harmful ultraviolet (UV) exposure. Melanin is a natural solar filter, absorbing and reflecting over 90% of the UV radiation passing through the horny layer of skin. Exposure to the sun for three days induces sufficient melanin production to multiply by ten the time required to experience sunburn.

The skin is a complex organ consisting of two basic layers, the epidermis and the underlying dermis (or corium), which are separated by the basal membrane. The epidermis includes a series of cellular strata, the uppermose of which is a horny surface layer of flattened cells that contain the tough, proteinaceous substance keratin. The horny layer plays a photoprotective role by reflecting substantial amounts of solar radiation. Beneath this layer is a layer of flattened cells containing granules of eleidin, the precursor of keratin. The granular layer overlies the Malpighi mucous layer, which, finally, overlies the bottommost basal layer. Melanocytes are found in the basal layer and exhibit generally globular cellular morphologies with numerous dendritic ramifications. These penetrate the neighboring keratinocytes of the basal layer and protect their DNA from any UV-induced modification. Melanocytes contain melanosomes, where melanin pigment is produced, and melanocyte dendrites release melanosomes onto the surroundings of neighboring cells, thereby diffusing pigmentation across the skin.

Melanosomes are small vesicles (0.5–2 $\mu$m in dark-skinned subjects and 2–8 $\mu$m in redhaired subjects) that bud from the intracellular Golgi apparatus of to melanocytes, producing melanin from the amino acid L-tyrosine through a sequence of chemical reactions. Critical to these reactions is the presence of the enzyme tyrosinase, which catalyzes the conversion of L-tyrosine to L-dihydroxyphenylalanine (L-Dopa). Tyrosinase is synthesized by ribosomes and reaches the melanosomes by intracellular diffusion. The melanosomes migrate from the Golgi apparatus through the cell body and into the dendrites, in the process accumulating melanin; by the time they are transferred to the surroundings of adjacent cells, the melanosomes have darkened considerably.

Melanin is a polymeric material that can take several chemical forms, the color of each form depending on its degree of oxidation. Eumelanins and *phaeomelanins,* both derived from L-Dopa, are the primary categories of melanin found in skin. Eumelanins are brown or black melanins with high molecular weights that exhibit a strongly networked polymeric structure. Formed by the polymerization of several hundreds of oxidized phenol radicals, eumelanins are amorphous and strongly absorb in the UV and visible spectral regions (resulting in their dark appearance). Phaeomelanins, by contrast, are much lighter in color (generally yellow to red/brown), reflecting smaller absorption of radiation, and are less highly crosslinked. Consequently, although they absorb UV radiation, the protection afforded by phaeomelanins is approximately 1000 times lower than that of eumelanins.

Normal individuals have both types of melanin; it is the difference in relative proportions of these that create differences in skin and hair coloration. The color of healthy human skin, or "constitutive skin pigmentation," results from the presence of red oxidized hemoglobin and blue reduced hemoglobin in the blood vessels of the dermis, as well as from the combination of melanins. Constitutive skin pigmentation represents a genetic trait, although only some hundreds of milligrams of melanin differentiate the darkest from the whitest skin colors. Suntans result from "adaptive pigmentation," the increase in melanin synthesis caused by exposure to UV radiation.

The primary factors in skin coloration are the nature of the melanin, the skin layer (epidermis or dermis) where the melanin is concentrated, and skin vascularization. Variations observed in melanocytes have little effect on normal skin pigmentation, which depends more directly on the quantity, type and distribution of melanosomes. Skin pigmentation anomalies, on the other hand, stem directly from the quantity of melanocytes. Hyperpigmentation patterns can reflect concentrations of correctly proliferating melanocytes, or the results of improper proliferation. The former category of pigmentation anomalies include freckles (eumelanin zones on phaeomelanin backgrounds), chloasma (a hypersecretion of melanin induced by hormonal factors and amplified by the effects of the sun), and various forms of hypermelanosis. Pigmentation anomalies resulting from melanocyte dysfunction include lentigines, solar and senile lentigo, Dubreuilh melanosis (a precancerous condition), moles and malignant melanomas.

Skin pigmentation can be reduced and excessive pigmentation prevented in three ways: by reducing the activity of tyrosinase, e.g., by using a competitive or noncompetitive tyrosinase inhibitor; by reducing melanocyte activity, e.g., with agents selectively cytotoxic for melanocytes; or by chemical reduction of L-Dopa to retard its oxidation into a chromophorous compound.

In the past, chemicals used to whiten skin—such as hydrogen peroxide, mercurialized amide chlorate, mercaptoamines and phenol derivatives such as hydroquinone and its catechol and alkyl-phenol esters—were harsh, irritative and not targeted to any particular stages of melanogenesis. Modern compositions are more selective in their effects and better tolerated by the skin. For example, placental extracts such as biomein inhibit the production of active tyrosinase by blocking its synthesis at the ribosomal level. Tunicamycine and glucosamine inhibit the transfer of tyrosinase to the pre-melanosomes by interrupting glycosylation. And kojic acid and ascorbic acid (as well as their derivatives) inhibit the enzymatic activity of tyrosinase.

Tyrosinase inhibition represents perhaps the optimal mechanism to reduce excessive pigmentation, since the observable effect is pronounced and quickly obtained with minimal side effects. Unfortunately, tyrosinase inhibitors such as kojic acid, ascorbic acid and their derivatives tend to be unstable in cosmetic preparations (due to high water content, significant variations in pH and temperature, and the presence of oxygen and numerous other chemical compounds). Their rapid oxidation decreases tyrosinase inhibition and results in the black or brown coloration of the cosmetic preparations. Moreover, although less cytotoxic than hydroquinone or linoleic acid, kojic and ascorbic acid products do exhibit some cytotoxicity.

DESCRIPTION OF THE INVENTION

Brief Summary of the Invention

The compositions of the present invention combine high tyrosinase blocking capabilities with stability in cosmetic preparations, absence of significant cytotoxic effects and synergy of action. Indeed, these compositions exhibit tyrosinase inhibition superior to a wide range of traditional agents at comparable concentrations. The active components of the invention include extracts of certain selected plants, namely, mulberry, saxifrage, grape and scutellaria root; and, preferably, ethylenediaminetetraacetic acid (EDTA). These ingredients interact synergistically to strongly inhibit tyrosinase activity; that is, the inhibition of the combined product is greater than what would be expected based on the inhibitions achieved by each component in isolation.

The ingredients are combined with various cosmetically acceptable carriers to produce cream and lotion formulations capable of whitening skin safely and effectively. These compositions, while very powerful in terms of tyrosinase inhibition, exhibit very low cytotoxicity-particularly when compared with currently available whitening compositions. The compositions of the present invention also exhibit good stability across varying temperature and pH levels; for example, a black or brown coloration is not observed even after 5 months at 45° C. and pH 5.5.

BRIEF DESCRIPTION OF THE DRAWING

The foregoing discussion will be understood more readily from the following detailed description of the invention, when taken in conjunction with the single FIGURE of the drawing, which compares the in vitro tyrosinase inhibition of the present invention against other known agents.

DETAILED DESCRIPTION OF THE PREFERRED EMBODIMENTS

1. Active Ingredients a. Mulberry Extracts

Extracts of mulberry have recognized vasoconstrictor and analgesic properties. In the present context, mulberry extract is believed to function as a source of phenylflavones and derivatives thereof (such as A, B and C kuwanones and morusin), which inhibit tyrosinase activity. The extracts also contain triterpenoids, such as α-amyrin and β-amyrin.

The mulberry extracts of the present invention can be obtained from the dried bark, roots or leaves of any of the 10 known species of mulberry; the *Morus nigra* species is preferred. Extracts are prepared by macerating the roots, leaves, tubers, flowers and/or fruits of the mulberry plant into a water/alcohol solution, the alcohol being selected from the group consisting of propylene glycol, butylene glycol, polyethylene glycols and ethanol; the preferred ratio of water to alcohol is 60%:40%, and the preferred alcohol is butylene glycol. The maceration is preferably performed at room temperature over a period of 1 to 15 days under gentle agitation. The macerate is filtered and is then ready for use. One or more preservatives (e.g., paraben-based preservatives) may also be added to the macerate.

b. Saxifrage Extracts

Useful saxifrage extracts can be obtained from the leaves or the whole plants of any of the 370 known species of saxifrage; *Saxifraga stolonifera* is preferred. Extracts are prepared by macerating the roots, leaves, tubers, flowers and/or fruits of the saxifrage plant into a water/alcohol solution, the alcohol being selected from the group consisting of propylene glycol, butylene glycol, polyethylene glycols and ethanol; the preferred ratio of water to alcohol is 60%:40%, and the preferred alcohol is butylene glycol. The maceration is preferably performed at room temperature over a period of 1 to 15 days under gentle agitation. The macerate is filtered and is then ready for use. One or more preservatives (e.g., paraben-based preservatives) may also be added to the macerate.

The principal active components of saxifrage extracts include tannins known as proanthocyanidins, which inhibit lipidic oxidation and trap free radicals, such as those generated by UV exposure; and arbutin, a natural molecule with a structure close to that of hydroquinone. The extracts preferably contain a maximum of 2% arbutin, and also include various long-chain alkanes (17–32 carbon atoms), terpenes and alcohols (e.g., camphene, linalool and boreol).

c. Scutellaria Root Extracts

Useful extracts can be obtained from the root of *Scutellaria baicalensis* (also known as oughon). The extracts contain flavonoids such as woogonin, baicalin and baicalein, which have known tyrosinase inhibitory activity.

Extracts are prepared by macerating the roots of the scutellaria plant into a water/alcohol solution, the alcohol being selected from the group consisting of propylene glycol, butylene glycol, polyethylene glycols and ethanol; the preferred ratio of water to alcohol is 60%:40%, and the preferred alcohol is butylene glycol. The maceration is preferably performed at room temperature over a period of 1 to 15 days under gentle agitation. The macerate is filtered and is then ready for use. One or more preservatives (e.g., paraben-based preservatives) may also be added to the macerate.

d. Grape Extracts

The grape extracts of the present invention can be obtained from virtually any grape species, although *Vitis vinifera* is preferred; the key ingredients of the extracts are various sugars and α-hydroxy acids (primarily tartaric acid).

Extracts are prepared by macerating the fruits of the selected grape plants into a water/alcohol solution, the alcohol being selected from the group consisting of propylene glycol, butylene glycol, polyethylene glycols and ethanol; the preferred ratio of water to alcohol is 60%:40%, and the preferred alcohol is butylene glycol. The maceration is preferably performed at room temperature over a period of 1 to 15 days under gentle agitation. The macerate is filtered and is then ready for use. One or more preservatives (e.g., paraben-based preservatives) may also be added to the macerate.

e. Ethylenediaminetetraacetic Acid (EDTA)

EDTA is widely used in pharmaceutical and cosmetic preparations as a chelating agent of metal ions, e.g., ionic forms of copper and iron. In the present invention, it functions to inhibit tyrosinase by trapping the cofactor $Cu^{++}$ required for the enzymatic oxidation of tyrosine. The disodium form of EDTA is preferred.

2. Formulations

A preferred formulation of active ingredients, referred to herein as the "Preferred Composition" of the invention, is as follows (in wt %):
saxifrage extract: 25–50%
grape extract: 25–50%
butylene glycol: 10–25%
water: 10–25%
mulberry extract: 1–5% scutellaria root extract: 1–5%
EDTA: 1–5%

The mixture is preferably stabilized and bacteriologically preserved with sodium sulfite (0–5%) and sodium metabisulfite (0–5%).

A useful skin whitening cream is formulated as follows:

| Process Step | Raw Material | INCI Denomination | wt % |
|---|---|---|---|
| Heat oily phase to 90° C. | Arlacel 165 | Glyceryl stearate, PEG 100 stearate | 4.00 |
| | Vegetable oil | Hydrogenated coconut oil | 2.50 |
| | Natural perhydro-squalane | Squalane | 2.50 |
| | Cetyl alcohol | Cetyl alcohol | 3.00 |
| | Fluid vaseline oil | Mineral oil | 6.00 |
| | Silicon oil 70047 V 300 | Dimethicone | 1.00 |
| | Emulgin B-2 | Ceteareth 20 | 3.00 |
| | Phenonip | Phenoxyethanol, methylparaben, ethylparaben, propylparaben, butylparaben BHA | 0.50 |
| Disperse in the melted oily phase | Organophilic titanium dioxide | Titanium dioxide Cl 77891 | 1.00 |
| Add the melted oily phase just before preparing the emulsion | Vitamin E acetate | Tocopheryl acetate | 0.20 |
| Heat to 90° C.. | Water | Water | 63.74 |
| Homogenize. Add the oily phase to the aqueous phase to make the emulsion. Cool. | Methylparaben Sodium polyphosphate Butylene glycol | Methylparaben Sodium hexametaphosphate Butylene glycol | 0.15 0.40 5.00 |
| Homogenize the Sepigel before weighing. Add to the cream at approximately 60° C.. Homogenize. | Sepigel 305 | Polyacrylamide, Isoparaffin, Laureth-7 | 3.00 |
| Add to the emulsion at approximately 55° C.. Homogenize. | Timiron super blue | Mica, titanium dioxide Cl 77019/ 77891 | 2.00 |
| Add in at 30° C.. | Preferred Composition | Active ingredient mixture | 2.00 |

The concentration of the active ingredient mixture can, however, be varied between 0.1% and 20%.

A useful skin-whitening lotion is formulated as follows:

| Process Step | Raw Material | INCI Denomination | wt % |
|---|---|---|---|
| Disperse with a turbine and heat the aqueous phase to 90° C. in the preparation tank. Ensure absence of lumps before continuing. | Water Keltrol T | Water Xanthan gum | 80.45 0.50 |
| Add to the previous phase at 90° C.. Ensure total solubilization. Cool. | Methylparaben Sodium polyphosphate | Methylparaben Sodium hexametaphosphate | 0.15 0.40 |
| Disperse in the previous phase at 60° C. using the turbine. | Techpolymer MB-4C | Polymethylmethacrylate | 1.00 |
| Homogenize the Sepigel before use. Add to the previous phase at approximately 45° C.. Turbine for proper homogenization until a milky solution is obtained. | Sepigel 305 | Polyacrylamide, Isoparaffin, Laureth-7 | 0.65 |
| Add at approximately 40° C.. Homogenize. | Silicon oil Q2 1401 | Dimethiconol, cyclomethicone | 2.00 |
| Dissolve. Add in at approximately 30° C.. Homogenize. | Sepicide Cl Water Butylene glycol | Imidazolidinyl urea Water Butylene glycol | 0.25 8.00 5.00 |
| Add in at 30° C.. | Preferred Composition | Active ingredient mixture | 2.00 |

The concentration of the active ingredient mixture can, however, be varied between 0.1% and 20%.

3. Efficacy Studies

Tyrosinase catalyzes the formation of L-dopaquinone, and then dopachrome (in the eumelanin pathway), from L-Dopa. Dopachrome is a colored compound and may be observed using UV-visible spectrophotometry at 475 nm. Comparisons in the rate at which this colored substance appears in the presence of a candidate whitening material indicate the effect of the material on enzymatic activity; complete absence of dopachrome reflects total inhibition of tyrosinase.

FIG. 1 illustrates the effect of different concentrations of the Preferred Composition, as well as various conventional skin-whitening materials (also tested at different concentrations). The tests demonstrate that hydroquinone, although approved as an over-the-counter whitening product, exhibits no tyrosinase-inhibiting activity. Its mechanism of action is not only different but cytotoxic, particularly on melanocytes. Ascorbic acid was found to inhibit 66% of tyrosinase activity at a concentration of 0.1%; kojic acid inhibited 71% and 80% of tyrosinase activity at concentrations of 0.1% and 1%, respectively. At these concentrations, however, ascorbic acid and kojic acid typically produce black or brown colorations in cosmetic preparations.

The activity of the present invention was observed at concentrations as low as 0.01%. At 1%, the Preferred Composition inhibited 97% of tyrosinase activity, and the efficacy rose to 100% at concentrations as low as 5%. No other tested material reached similarly high efficacy levels at relatively low concentrations, or exhibited such pronounced increases in efficacy level with concentration.

The anti-tyrosinase activity of the invention was also evaluated using an ex vivo tissue model by exposing human skin explants to the material. The explants were obtained from a 27-year-old female patient who underwent abdominal plastic surgery. In this assay, intramelanocyte antityrosinase activity was evaluated by exposing the explant, following subjection to the Preferred Composition, to an L-Dopa solution. Oxidation of L-Dopa by tyrosinase produces in the melanocyte an observable black pigment, which can easily be detected by optical microscopy. Tyrosinase activity can be measured by the intensity of the observed coloration.

The solutions of the Preferred Composition to which explants were exposed included 0.1%, 1% and 10% (v/v) solutions in ultrapure water. A positive control and a negative control were also conducted in the same experiment. Hydroquinone at 0.55% (w/v) was selected as the positive control; although hydroquininone does not inhibit tyrosinase, it does counteract melanin pigment formation in melanocytes, thereby producing similar observable effects. The explants, each exposed to a different test solution, were incubated with L-Dopa (0.05M) for 15 hours at 37° C. After fixation and inclusion in paraffin, the skin slices were colored with hemalun/eosin/safran and cresyl violet, and observed by optical microscopy under white light.

It was found that the three concentrations of the Preferred Composition completely inhibited the formation of melanin, as did the hydroquinone (although via a different mechanism). The depigmenting effect of the Preferred Composition was quite pronounced, since a concentration of 0.1% produced results identical to that achieved with 0.55% hydroquinone.

Hydroquinone, of course, is cytotoxic to melanocytes. To evaluate the cytotoxicity of the Preferred Composition, melanocyte cell line G361 (human melanome) was cultivated in MacCoy Medium (obtained from GIBCO) supplemented with 10% fetal calf serum, 500 Ul/ml penicillin, 50 $\mu$g/ml streptomycin and 2 mM glutamin. Test wells were seeded at $3\times10^5$ cells/well, suspended in the aforementioned medium and the Preferred Composition added at different concentrations. After incubating for 72 hours, cell viability was evaluated by a protein assay with a BIO-RAD kit. The onset of cytotoxicity occured between 1 and 10 mg/ml of the Preferred Composition—well above the concentrations necessary for skin whitening. This concentration compares quite favorably with the $IC_{50}$ concentrations (which kill more than 50% of the cells in a culture) reported for other skin whiteners: the $IC_{50}$ of hydroquinone is $5.5\times10^{-3}$ mg/ml, the $IC_{50}$ of linoleic acid is $2.8\times10^{-3}$ mg/ml, and the $IC_{50}$ of ascorbic acid is 0.88 mg/ml.

The tyrosinase inhibition of the Preferred Composition substantially exceeds what would be expected based on the inhibitory levels of the individual components in isolation. These were evaluated separately and the following results obtained:

| Saxifrage Extract Concentration (%) | Tyrosinase Inhibition (%) |
|---|---|
| 100 | 88 |
| 50 | 76 |
| 10 | 62 |
| 2 | 28 |
| 0 | 0 |

| Mulberry Extract Concentration (%) | Tyrosinase Inhibition (%) |
|---|---|
| 100 | 72 |
| 50 | 61 |
| 20 | 35 |
| 10 | 25 |
| 2 | 0 |

| Scutellaria Root Extract Concentration (%) | Tyrosinase Inhibition (%) |
|---|---|
| 50 | 45 |
| 5 | 25 |
| 0.5 | 0 |

| Grape Extract Concentration (%) | Tyrosinase Inhibition (%) |
|---|---|
| 5 | 85 |
| 1 | 87 |
| 0.1 | 0 |

| EDTA Concentration (%) | Tyrosinase Inhibition (%) |
|---|---|
| 5 | 78.9 |
| 1 | 47.3 |
| 0.1 | 0 |

Because arbutin is present at a concentration of about 2% in saxifrage extract and because arbutin is known to be very active in tyrosinase inhibition, it is consider the activity of pure arbutin:

| Pure Arbutin (%) | Tyrosinase Inhibition (%) |
|---|---|
| 5 (max. solubility) | 45 |
| 2.5 | 35 |
| 0.5 | 25 |
| 0.2 | 20 |
| 0 | 0 |

Accordingly, the activity of the invention cannot be explained merely by the presence of arbutin.

It will therefore be seen that the foregoing represents a highly effective yet well-tolerated and cosmetically stable approach to skin depigmentation. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A composition for inhibiting formation of unwanted pigmentation, the composition comprising:
   a. a mulberry extract;
   b. a saxifrage extract;
   c. a scutellaria extract;
   d. a grape extract; and
   e. ethylenediaminetetraacetic acid.

2. The composition of claim 1 wherein the composition further comprises:
   a. saxifrage extract in the range 25–50 wt %;
   b. grape extract in the range 25–50 wt %;
   c. mulberry extract in the range 1–5 wt %;
   d. scutellaria extract in the range 1–5%;
   e. ethylenediaminetetraacetic acid in the range 0.1–5%;
   f. sodium sulfite in the range 0–5%; and
   g. sodium metabisulfite in the range 0–5%.

3. The composition of claim 2 wherein the composition further comprises:
   a. 25 wt % saxifrage extract;
   b. 30 wt % grape extract;
   c. 5 wt % mulberry extract;
   d. 5% scutellaria extract;
   e. 0.5 wt % ethylenediaminetetraacetic acid;
   f. 1% sodium sulfite; and
   g. 1% sodium metabisulfite.

4. The composition of claim 1 wherein the mulberry extract is derived from *Morus nigra*.

5. The composition of claim 1 wherein the saxifrage extract is obtained from *Saxifraga stolonifera*.

6. The composition of claim 1 wherein the scutellaria extract is obtained from the root of *Scutellaria baicalensis*.

7. The composition of claim 1 wherein the grape extract is obtained from *Vitis vinifera*.

8. A cream comprising the composition of claim 1 and a carrier.

9. The cream of claim 8 wherein the composition is present in the cream at a concentration ranging from 0.1 to 20%.

10. A lotion comprising the composition of claim 1 and a carrier.

11. The lotion of claim 10 wherein the composition is present in the lotion at a concentration ranging from 0.1 to 20%.

12. A method of inhibiting formation of unwanted pigmentation, the method comprising:
   a. providing a composition comprising:
      i. mulberry extract;
      ii. a saxifrage extract;
      iii. a scutellaria extract;
      iv. a grape extract; and
      v. ethylenediaminetetraacetic acid; and
   b. applying the composition to an area of skin, thereby inhibiting tyrosinase function within the area.

13. The method of claim 12 wherein the composition comprises:
   a. saxifrage extract in the range 25–50 wt %;
   b. grape extract in the range 25–50 wt %;
   c. mulberry extract in the range 1–5 wt %;
   d. scutellaria root extract in the range 1–5%; and
   e. EDTA in the range 0.1–5%;
   f. sodium sulfite in the range 0–5%; and
   g. sodium metabisulfite in the range 0–5%.

14. The method of claim 13 wherein the composition comprises:
   a. 25 wt % saxifrage extract;
   b. 30 wt % grape extract;
   c. 5 wt % mulberry extract;
   d. 5% scutellaria root extract;
   e. 0.5 wt % EDTA;
   f. 1% sodium sulfite; and
   g. 1% sodium metabisulfite.

15. The method of claim 12 wherein the mulberry extract is derived from *Morus nigra*.

16. The method of claim 12 wherein the saxifrage extract is obtained from *Saxifraga stolonifera*.

17. The method of claim 12 wherein the scutellaria extract is obtained from the root of *Scutellaria baicalensis*.

18. The method of claim 12 wherein the grape extract is obtained from *Vitis vinifera*.

19. The method of claim 12 wherein the composition is formulated as a cream.

20. The method of claim 1 wherein the composition is formulated as a lotion.

* * * * *